US005556789A

United States Patent [19]

Goerlach-Graw et al.

[11] Patent Number: 5,556,789

[45] Date of Patent: Sep. 17, 1996

[54] DEVICE FOR THE SIMULTANEOUS DETERMINATION OF SEVERAL ANALYTES

[75] Inventors: Ada Goerlach-Graw, Grosskarlbach; Reinhard Baer, Mannheim; Rolf Lerch, Ilvesheim, all of Germany

[73] Assignee: Boehringer Mannheim GmbH, Mannheim, Germany

[21] Appl. No.: 270,162

[22] Filed: Jul. 1, 1994

[30] Foreign Application Priority Data

Jul. 15, 1993 [DE] Germany .......................... 43 23 672.3

[51] Int. Cl.[6] .................................................... G01N 33/00

[52] U.S. Cl. ............................ 436/169; 436/63; 436/807; 436/901; 422/58; 422/56

[58] Field of Search .................................... 436/165, 169, 436/901, 63, 807; 422/56–58, 61; 435/7.1, 810

[56] References Cited

U.S. PATENT DOCUMENTS

| | | | |
|---|---|---|---|
| 4,323,536 | 4/1982 | Columbus | 422/56 |
| 5,051,237 | 9/1991 | Grenner et al. | 422/56 |
| 5,110,724 | 5/1992 | Hewett | 435/11 |
| 5,149,505 | 9/1992 | English et al. | 422/99 |
| 5,215,713 | 6/1993 | Steinbiss | 422/61 |
| 5,238,652 | 8/1993 | Son et al. | 422/61 |
| 5,238,847 | 8/1993 | Steinbiss et al. | 436/64 |
| 5,354,538 | 10/1994 | Bunce et al. | 422/100 |

FOREIGN PATENT DOCUMENTS

| | | |
|---|---|---|
| 374684 | 6/1990 | European Pat. Off. . |
| 511120 | 10/1992 | European Pat. Off. . |
| 8100302 | 2/1981 | WIPO . |
| 8807666 | 10/1988 | WIPO . |
| 9011830 | 10/1990 | WIPO . |
| 9310456 | 5/1993 | WIPO . |

*Primary Examiner*—James C. Housel
*Assistant Examiner*—Rachel Heather Freed
*Attorney, Agent, or Firm*—Felfe & Lynch

[57] ABSTRACT

Device for the determination of analytes having a sample application point, several separate sample withdrawal zones that are each connected with the sample application point by one capillary transport path and that have several test elements for the individual determination of analytes wherein a retardation zone is provided on at least one of the transport paths. Material for the capillary transport of a liquid sample defines a sample application zone and a plurality of sample withdrawal zones connected to said application zone by a like plurality of transport paths. At least one of said paths has a retardation zone which assures that liquid applied to said application zone arrives simultaneously at said withdrawal zones, regardless of the lengths of the paths.

10 Claims, 3 Drawing Sheets

Area F1 = Area F2 = Area F3

DEVICE FOR THE SIMULTANEOUS DETERMINATION OF SEVERAL ANALYTES

BACKGROUND OF THE INVENTION

The invention concerns a method for the determination of several analytes in a multizone device as well as a device which is suitable therefor.

A recent development in medical diagnostics is to facilitate the diagnosis by the attending physician or by the patient himself of disease states by the detection of characteristic analytes in body fluids. When the clinical pictures are complex or when the cause of a disease cannot yet be exactly localized, it is often advisable or even necessary to carry out the determination of several different analytes. Thus for example in the case of tests for drug abuse individual tests for many drugs have to be carried out because of the multitude of possible drugs and the often unknown case history of the patient. Similar problems occur for example when diagnosing kidney and thyroid diseases or infectious diseases.

The so-called dry tests have proven to be reliable for the rapid and simple determination of analytes. In these a reagent or a multitude of reagents in dry form is located on a capillary carrier which is brought into contact with the sample liquid in order to carry out the test. The reagents dissolve in the liquid and give a characteristic signal for the analyte such as a change in colour, on the basis of which an analysis can be carried out. In simple tests it is sometimes possible to arrange the capillary carriers containing reagents on a single test element which is then immersed in the liquid in such a way that all carriers are wetted by the liquid. An example of such test elements is urea test strips which contain test zones for several analytes e.g. leucocytes, density, pH etc..

However, such a simple procedure of immersing the test zones once is for example not possible for immunological determinations of analytes such as antigens, haptens, and antibodies since these determinations are processes with a multistep reaction sequence. In this case the liquid containing the analyte passes along a test path containing several zones on which an exchange takes place of the various reagents between the liquid and the test zones. In one zone towards the end of the test path a characteristic signal for the presence of the analyte can be obtained and analysed.

In EP-A-0 467 175, to which U.S. Pat. No. 5,215,713 a method and a device are proposed for the determination of several analytes from a paste-like sample e.g. stool. The device contains an eluant application zone and several eluate transfer agents which ensure fluid contact with test strips for the desired determinations. Between the eluant application zone and the eluate transfer agents there is a region for the application of the paste-like sample. Between the eluant application zone and the sample application area there is a transport path for the pure eluant which is designed in such a way that the eluant flow is considerably retarded by the sample in order to achieve an effective elution of the relatively heterogeneous solid sample. Firstly the pure eluant is applied to this eluant application zone and is transported from there to the sample application area without change in the components. After elution of the analyte from the sample in the sample application area the eluate which now contains analyte flows through a transport zone which widens towards the test carriers wherein the transport paths are not separated from one another. The method described in EP-A-0 467 175 has the disadvantage that the various test strips and thus also the reagents come into contact with the eluate at different times and consequently in some cases different test results are obtained for the same test strips when using different eluate transfer agents. This can be particularly disadvantageous for a quantitative evaluation of analyses. Moreover the problems increase with an increasing number of eluate transfer agents..

SUMMARY OF THE INVENTION

The object of the invention is to provide a method and a device for the determination of analytes contained in a liquid which enables an essentially simultaneous and uniform determination of the analytes at various withdrawal sites on several test elements. The invention therefore concerns a device for the determination of analytes containing

- a sample application point,
- several separate sample withdrawal zones each of which are linked by a respective transport path with the sample application point,
- several test elements for the individual determination of analytes, wherein a retardation zone is provided on at least one of the transport paths.

Analytes of the method according to the invention are above all components of body fluids such as urine, blood, serum, saliva, sweat or plasma or fluids derived therefrom (e.g. diluted with water, buffers or alcohols) or other liquids such as e.g. solutions of powders which are to be tested for drug content.

A preferred body fluid is urine. Preferred analytes are dissolved chemical substances whose presence or absence or concentration in the respective body fluid indicates a disease or a physical condition. Analytes which are immunologically detectable are particularly preferred i.e. haptens, antigens or antibodies, but also nucleic acids and other biospecifically detectable substances. Preferred analytes in urine are drugs such as cocaine, cannabis (hashish) or opiates (heroin) or kidney parameters such as albumin, $\alpha$-1M, $\beta$-NAG.

The device according to the invention has at least four zones which are capillary-actively connected with one another i.e. two or more transport zones and two or more sample withdrawal zones. In addition it contains a sample application point.

The sample application point preferably lies on a capillary fleece or fabric which is chemically inert towards the sample liquid. It is preferably delineated by an appropriate mark e.g. by applying visible symbols such as circles, crosses, arrows etc. or by a constructional separation e.g. by covering the fleece surrounding the application point.

The transport zones extend from the sample application point up to the sample withdrawal zones. A device according to the invention preferably has as many transport zones as sample withdrawal zones whereby the transport zones are separated spatially from one another at least in the vicinity of the sample withdrawal zone so that no liquid can pass from one transport path to another. The transport zones are made of capillary material and are in particular constructed of a capillary fleece or fabric which is chemically inert towards the sample liquid. A transport zone is understood in the following as an area over which a flat material extends which is capable of liquid uptake. This material has a thickness which is less than the width and length of the area. The sample liquid flows through the length of each transport zone. The transport zones are either spatially separated from one another or their mutual boundaries are fashioned in such a way that segments of the liquid volumes within the transport zones move towards the respective sample withdrawl zone.

The sample withdrawal zone is understood as an area of the device which is likewise capillary-active which is in a configuration with a test element enabling liquid contact or can be brought into such a configuration. As soon as the sample withdrawal zone receives liquid from the transport zone, the liquid can pass over onto the adjoining test element.

A capillary volume is defined by the suction volume of the transport zones and sample withdrawal zones. This volume is less than or at most equal to the volume of the applied sample liquid. The volume of the applied liquid which exceeds the capillary volume is preferably as large as the additional suction volume of the test elements adjoining the sample withdrawal zone.

The paths along which a particular liquid volume travels between the sample application point and the sample withdrawal zone are denoted transport paths in the following. The applied sample liquid is not altered on these transport paths at least with regard to the analytes.

Fleeces made of synthetic fibres (e.g. polyester) which if desired can be admixed with cellulose fibres are particularly suitable as the capillary-active material. Such materials are well-known for the construction of test strips. The fleeces are preferably between 0.35 and 1.5 mm thick.

An essential feature of the invention is that a retardation zone is provided on at least one of the transport paths. The retardation zone is preferably located in the transport zone. The effect of the retardation zone is that the stream of liquid does not pass so rapidly from the sample application point to the respective sample withdrawal zone as when there is no retardation zone. A first possibility of achieving the retardation is to make the transport paths which lead to the different sample withdrawal zones of equal length. A second possibility is to make the areas of the transport zones equally large. In order to achieve equally long transport paths it may be necessary to extend one or several transport paths relative to the shortest distance between the sample application point and sample withdrawal zone or to introduce one or several hydrophobic barriers. The following measures are in principle suitable for producing equal volumes:

1. (Horizontal) extension of the width of the material of the transport zone at at least one position in comparison to another transport zone,
2. (Vertical) contraction of the thickness of the material of the transport zone at at least one position compared with another transport zone,
3. Reduction of the flow cross-section on the transport routes by constriction of the material of the transport zone at at least one position compared with another transport zone.

These measures can also be combined with one another.

In particular when it is not possible (e.g. if very many sample withdrawal zones are present) to ensure the desired retardation by using equally large volumes, it is recommended that the flow cross-section should be reduced on one or several transport paths or to place hydrophobic barriers.

The shorter distance between sample application point and sample withdrawal zone, the larger the effected retardation has to be. If the shortest distances between various sample withdrawal zones and the sample application point are of equal length, then the effected retardations must also be of approximately equal magnitude on all transport paths.

A test element is understood as a means to detect the presence or the amount of an analyte by which means preferred elements are constructed in the manner of test strips. This means that they have a supporting foil on which absorptive materials are attached on which the reagents that are necessary for the test are applied. Such a test element is described for example in EP-A-0 374 684. When such a test element is contacted with the sample withdrawal zone this is preferably achieved via a zone of the test element which does not yet contain any reagents. If it is intended to use a test carrier according to EP-A-0 374 684 for the determination of an analyte the start zone 21 described in this application is contacted with a sample withdrawal zone 4 of the device according to the invention. In order to determine several analytes simultaneously, as many test elements are contacted with the sample withdrawal zones as the number of determinations which are necessary.

An advantage of the device according to the invention is that a flooding of the test elements with sample liquid is avoided by the retardation zones. In addition the simultaneous contacting of the test carriers with the sample liquid has the effect that no reagent carrier receives more liquid than another. Since in order to reliably carry out determinations it is often necessary to read a signal from the test element within a certain time period after contacting the test element with the sample liquid, the fact that the liquid front reaches all sample withdrawal sites at the same time according is a major advantage of the present invention. Another effect of the simultaneous arrival of the liquid is that the test elements for different analytes do not necessarily have to be mounted in the device in an order matching the respective sample withdrawal sites, but rather that they are interchangeable. This is of particular importance in the case of determinations in which the users can themselves carry out determinations as required. A further advantage of the uniform wetting is that test elements for the determination of several analytes can be arranged in profiles as required. Thus by using appropriate test elements the device according to the invention can for example be used either to prepare a kidney function profile i.e. determine several analytes that are characteristic for kidney function or a drug profile e.g. the determination of several common drugs (drugs of abuse). The device according to the invention can therefore be sold in a form in which the test elements are already connected to the sample withdrawal zones e.g. by inclusion of the test elements in the housing or can be sold in a form in which the housing together with the sample application zone, the transport path and the sample withdrawal zone is one component and a number of test elements are in another container and can be inserted into the housing by the person who wishes to carry out the analysis.

DETAILED DESCRIPTION OF THE PREFERRED EMBODIMENTS

Figure 1:
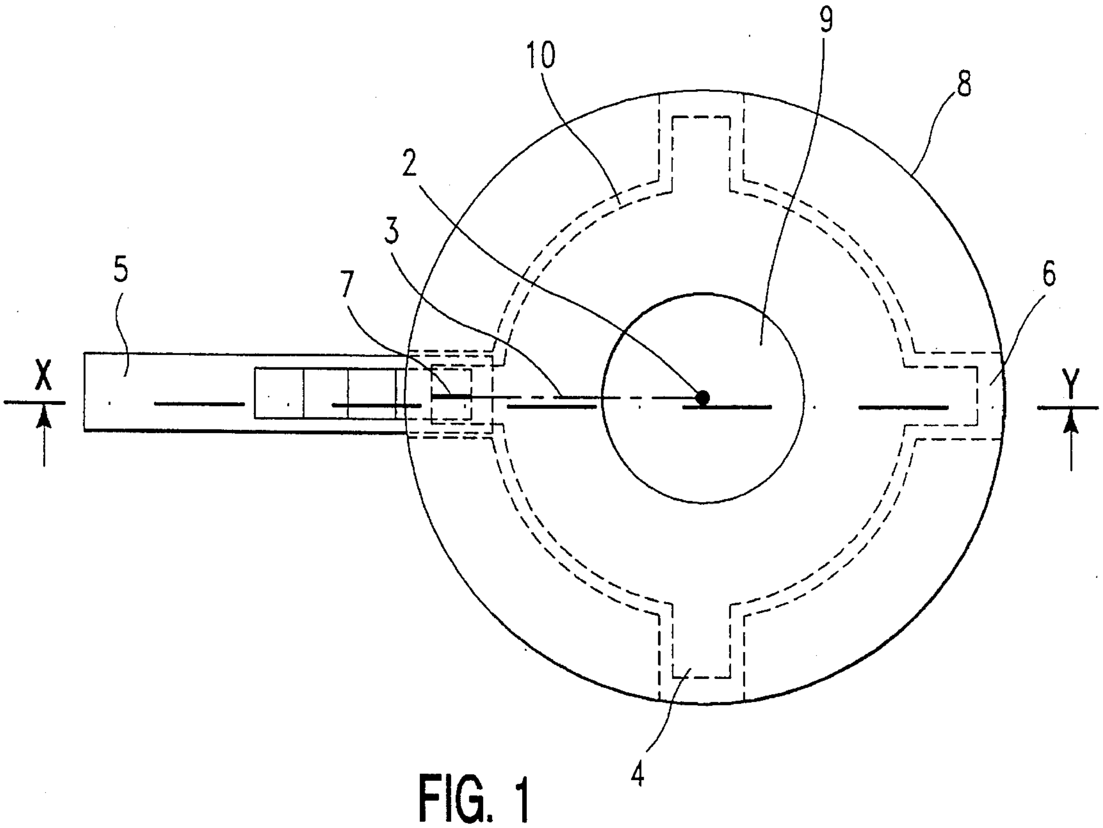
FIG. 1 shows a device where the withdrawal zones are in a radial arrangement around the sample application zone.

Two embodiments have turned out to be preferable for the device. In the first form, the sample withdrawal zones 4 are in an essentially complete or partially radial arrangement around the sample application point 2 (FIG. 1). In a particularly preferred case the shortest connecting paths are then of equal length. The transport paths can then firstly lead through a radially symmetric, capillary-active fleece and then in parallel through as many fleeces as there are sample withdrawal zones. The latter fleeces are designed in such a way that no liquid flow is possible between them. They can for example be fashioned in the form of connectors which extend from the edge of the sample application fleece to the sample withdrawal zones. The material of the connectors preferably overlaps a little with the sample application fleece so that when the materials are compressed in the housing 8 at the site of overlap, sites are formed with a smaller flow cross-section that act as a retardation zone 7. The overlapping site is preferably ca. 1 to 2 mm wide. In the example shown in FIG. 1, the retardation on all transport paths (3) is of the same magnitude. If the sample liquid is not exactly dispensed on the sample application point 2 through the housing opening 9, the liquid—after reaching the retardation zone on the shortest transport path—will firstly flow up to the retardation zones of the other transport paths until the capillary pressure is equal at all retardation zones. Then the liquid will pass essentially simultaneously through all retardation zones to the recesses 6 for the test elements 5. Since the adjoining parts of the transport paths are of the same length and have the same composition, the liquid will reach the test elements at the same time. The ends of the transpot paths which are equally distal to the application site can themselves even represent the sample withdrawal zones or separate fleeces can be provided for this. The test elements 5 are in capillary contact with the sample withdrawal zones 4 because the contour of the capillary-active fleece 12 (10) overlaps the test element fleece 12. In this embodiment a flooding of the test strips is in particular prevented.

Figure 2:
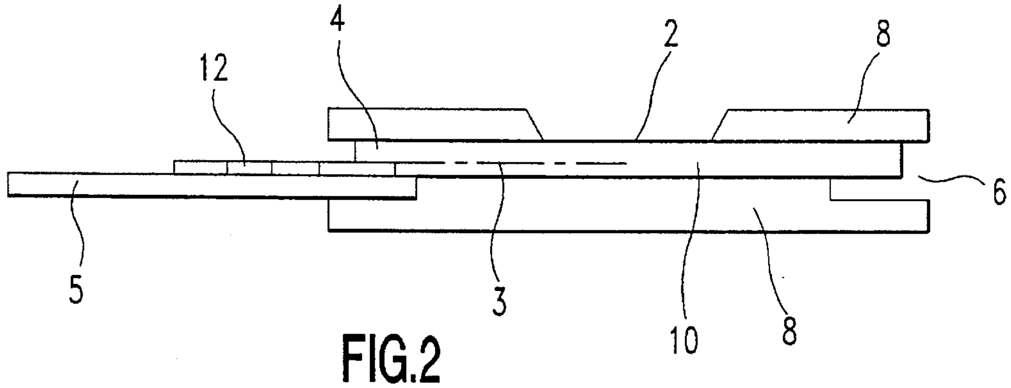

FIG. 2 shows the device of FIG. 1 in section X–Y. The reference numerals of FIG. 1 apply.

In a second embodiment (FIG. 3) which is easier to operate, the sample withdrawal zones 4 lie on an imaginary straight line so that all test elements 5 point essentially in the same direction. In this case the retardation effect of the retardation zones differs when the sample withdrawal zones are at different distances from the sample application point 2. Since liquids would spread radially in uniform capillary-active materials if there was no retardation zone, the liquid would firstly arrive at the sample withdrawal site 4/I that is nearest to the sample application point and would pass over onto the test element. The retardation must therefore be greatest on this transport path. The more distant the other sample withdrawal sites 4/II and 4/III are from the sample application point 2, the less the retardation has to be. Also in this case the transport paths 3/I, 3/II and 3/III preferably pass partially through connectors of fleece material.

The materials from which the transport zones and the sample withdrawal zones are made are located in a housing. This housing has an orifice 9 in the region of the sample application point so that the sample liquid can be applied to the material under the sample application point. The housing has additional openings 6 in the region of the sample withdrawal zones in which the test elements can be inserted so that the fleeces or fabrics of the test elements come into contact with the material of the sample withdrawal zone. Any material that is impermeable to the sample liquid can be used as the material for the housing e.g. one which is composed of a plastic or a paper impregnated against absorption of moisture.

Figure 4:
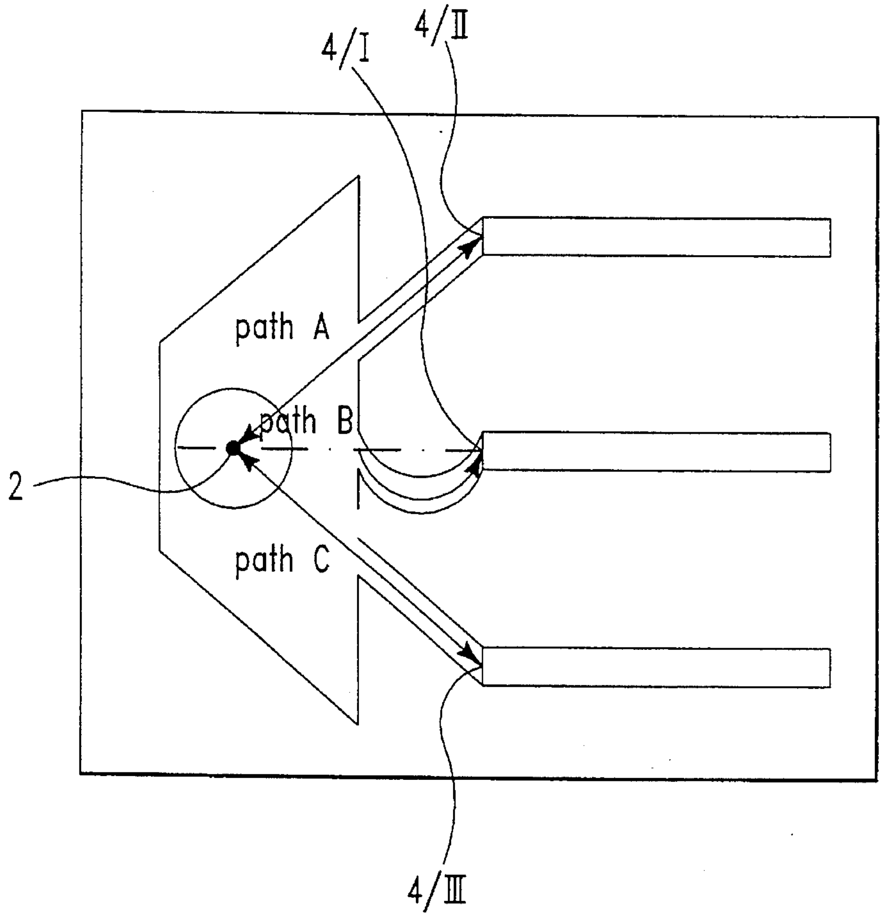

FIG. 4 shows how a retardation of the stream of liquid from the sample application point 2 to the sample withdrawal zones 4/I, 4/II and 4/III can be achieved. The simultaneous wetting of the sample withdrawal zones 4 is achieved in that path B does not represent the shortest transport path of the liquid but is elongated in comparison, so that paths A, B and C are of about the same length.

Figure 5:
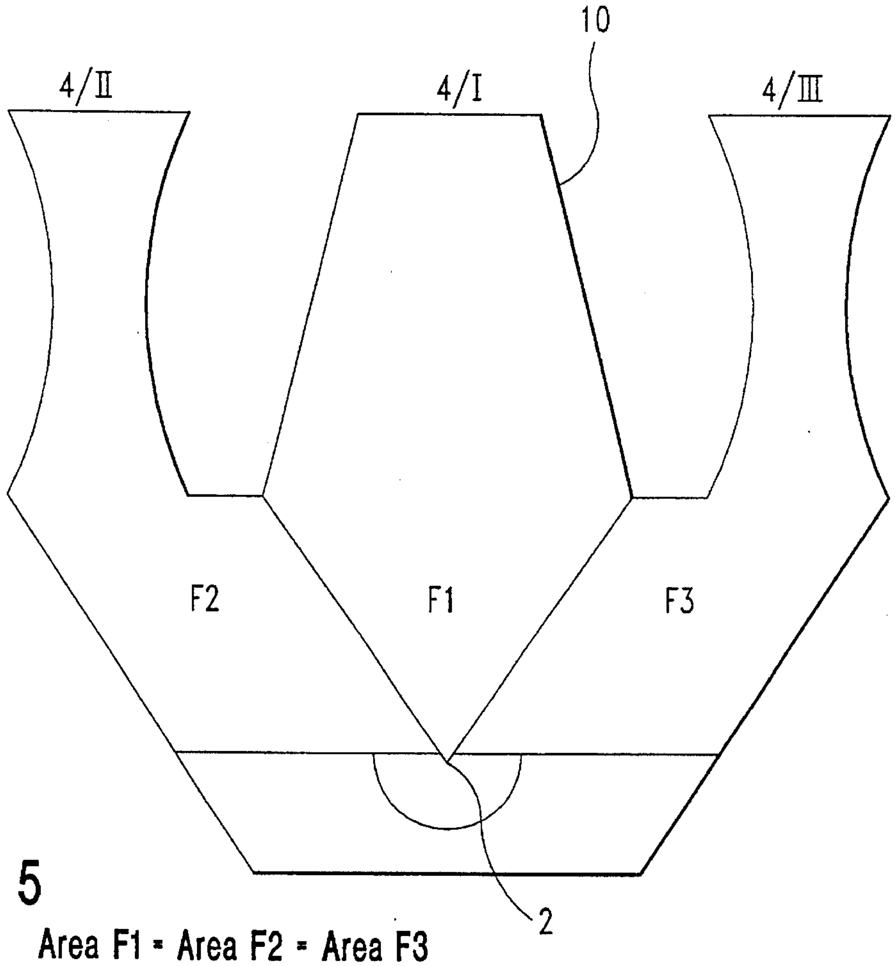

FIG. 5 shows how a shape of the capillary-active material which is suitable for simultaneous wetting of the sample withdrawal sites 4/I, 4/II and 4/III can be determined. The areas F1, F2 and F3 through which the sample liquid flows on its route to the individual sample withdrawal sites and which are located between the sample application point and sample withdrawal zone are essentially of the same area for this. In this case, when the areas are equal, the material and its thickness are the same for all transport paths.

Figure 6:
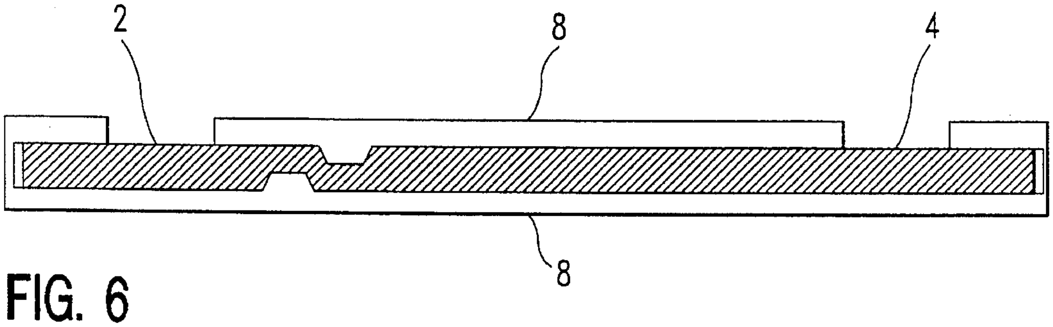

FIG. 6 shows the material on a transport path from the sample application point 2 to the withdrawal zone 4 in which a retardation of the liquid flow is achieved by vertical constriction, in this case by constant light compression of the fleece material. The pressure can be produced by cross-pieces which are facing one another or staggered in the bottom and/or lid component of the housing 8. The height of the cross-pieces can be utilized to produce a different transport retardation on different transport paths.

Figure 7:
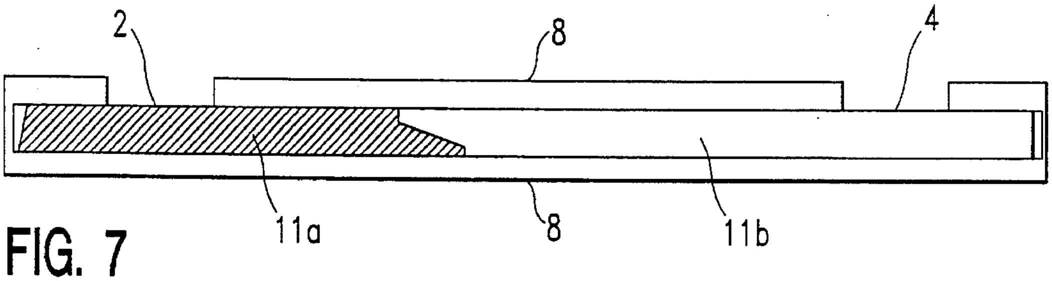

FIG. 7 shows a cross-section of a transport path in which the constituent materials (11*a*, 11*b*) which can be the same or different at the sample application point 2 and sample withdrawal zone 4 overlap. When there is a constant space between the lid and bottom component of the housing 8, a pressing overlap is achieved which in turn causes a retardation. The effect can be amplified by additional inert materials.

In the case of a retardation by hydrophobic barriers there are at least two possibilities which can in principle be envisioned. The impregnation of an absorptive material through which the liquid has to pass with a temporarily or permanently hydrophobizing substance (e.g. needle impregnation of 5 mm width with 3% Mowiol/polyvinylalcohol solution) retards the liquid flow. In a second method, a material of higher hydrophobicity (e.g. a paper or a membrane) can be incorporated into the transport path. Such hydrophobic barriers can be integrated at any desired position between the sample application zone and the first reagent zone in the test strip.

In a method according to the invention for the determination of several analytes contained in a sample liquid, the sample liquid is applied to a single sample application point. This can for example be achieved by pipetting or adding the liquid dropwise. The volume of applied liquid is preferably approximately equal to or somewhat more than the capillary-active volume of the entire device. The liquid migrates by capillary transport along the transport paths to several sample withdrawal zones. Retardation of the liquid transport on the transport paths that are nearest to the sample application point leads to a simultaneous wetting of the test elements.

The following examples are intended to elucidate the invention in more detail:

EXAMPLE

Figure 3:
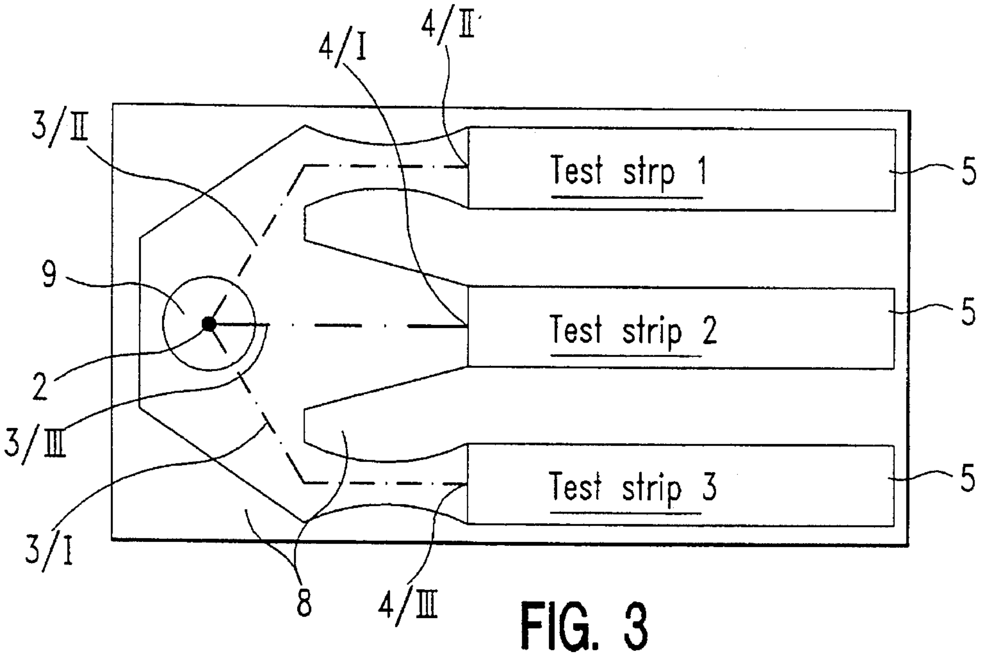

A piece of paper with the contours 10 of FIG. 3 is cut out of a TI 532 (Binzer Company) paper. This piece of paper is placed in the housing half-member 8 manufactured by means of injection moulding from polystyrene which contains recesses for the contour of the paper as well as for the test strips 5. Subsequently the test strips 5 (for example Mikral® test strips from Boehringer Mannheim GmbH) are inserted in such a way that the start fleece or the first fleece on which reagents are located is in direct contact with the sample withdrawal zones 4. Afterwards a second housing half-member is glued on which contains no recesses for the paper or the test strips but which has a recess in the vicinity of the sample application point 2 through which the sample liquid can be applied to the sample application point. The entire device has a length of ca. 15 cm, a width of 7 cm and a thickness of 0.5 cm.

In order to carry out a test for several analytes in a sample, ca. 10 ml urine is pipetted onto the sample application point. After a pre-determined period which depends on the reagents on the inserted test strips, the colour which has developed up to this time is compared with a comparative scale and from this a value for the presence or the amount of the analyte is taken.

If only 2–3 ml sample liquid is available, the dimensions of the capillary-active material should be approximately halved.

The same procedure can also be used to manufacture and use the device shown in FIGS. 1 and 2.

| List of reference symbols | |
|---|---|
| 1 | device according to the invention |
| 2 | sample application point |
| 3 | transport path |
| 4 | sample withdrawal zone |
| 5 | test element |
| 6 | recess for test element |
| 7 | retardation zone |
| 4/i, 4/II 4/III | sample withdrawal zones |
| 8 | housing |
| 9 | housing opening |
| 10 | contour of the capillary-active fleece |
| F1, F2, F3 | areas of the capillary-active material between 2 and 4 |

We claim:

1. Device for delivery of a liquid sample to multiple withdrawal zones at substantially the same time, said device comprising a plurality of sample withdrawal zones, fibrous capillary active transport means comprising a sample application zone and a plurality of transport paths connecting respective said sample withdrawal zones to said sample application zone, said fibrous capillary active transport means being free of reagents which react with analytes to be determined, and retardation means provided in at least one of said transport paths and arranged so that liquid sample applied to said sample application zone arrives simultaneously at each of said sample withdrawal zones.

2. Device as in claim 1 wherein said transport paths all have the same length.

3. Device as in claim 1 wherein said transport paths extend radially from said application zone.

4. Device as in claim 1 wherein said transport paths do not have the same length.

5. Device as in claim 4 wherein at least one of said transport paths does not have retardation means therein, said retardation means in the at least one of the other transport paths comprising a smaller cross section than the cross section of said at least one transport path without retardation means.

6. Device as in claim 4 wherein said retardation means comprises fibrous capillary active material that retards liquid transport as compared to the rest of the transport path in which said retardation means is provided.

7. Device as in claim 1 wherein said transport paths do not all have the same length, said paths including a shortest path having retardation means and at least one longer path having no retardation means.

8. Device as in claim 1 wherein said fibrous capillary active transport means is a fleece.

9. Device as in claim 1 wherein said fibrous capillary active transport means is a fabric.

10. Method for the determination of several analytes contained in a liquid sample, said method comprising the steps of providing fibrous capillary active transport means comprising a sample application zone, plurality of sample withdrawal zones spaced from said sample application zone, a plurality of transport paths connecting respective said sample withdrawal zones to said sample application zone, and retardation means provided in at least one of said transport paths and arranged so that liquid sample applied to said sample application zone arrives simultaneously at each of said sample withdrawal zones, and wherein said fibrous capillary active transport means is free of reagents which react with analytes to be determined, applying liquid sample comprising analytes to said application zone, contacting test elements containing reagents to at least two of said sample withdrawl zones, said reagents reacting with said analytes to produce observable results, and determining said analytes in accordance with said results.

* * * * *

UNITED STATES PATENT AND TRADEMARK OFFICE

CERTIFICATE OF CORRECTION

PATENT NO. : 5,556,789

DATED : September 17, 1996

INVENTOR(S) : Goerlach-Grav et al.

It is certified that error appears in the above-identified patent and that said Letters Patent is hereby corrected as shown below:

In column 3, line 62, between "shorter" and "distance", insert - - the - -.

In column 4, line 27, delete "according".

Signed and Sealed this

Eleventh Day of July, 2000

Attest:

Q. TODD DICKINSON

Attesting Officer

*Director of Patents and Trademarks*